US006368573B1

(12) United States Patent
Leung

(10) Patent No.: US 6,368,573 B1
(45) Date of Patent: Apr. 9, 2002

(54) DIAGNOSTIC USES OF 2-SUBSTITUTED ADENOSINE CARBOXAMIDES

(75) Inventor: Edward Leung, Cary, NC (US)

(73) Assignee: King Pharmaceuticals Research and Development, Inc.

( * ) Notice: Subject to any disclaimer, the term of this patent is extended or adjusted under 35 U.S.C. 154(b) by 0 days.

(21) Appl. No.: 09/440,330

(22) Filed: Nov. 15, 1999

(51) Int. Cl.$^7$ ............... A61K 49/00; C07H 1/00
(52) U.S. Cl. ............ 424/9.1; 424/569; 424/9.2; 536/1.1
(58) Field of Search ............ 424/9.1, 569, 9.2; 536/1.1

(56) References Cited

U.S. PATENT DOCUMENTS 5,206,222 A * 4/1993 Forman et al. ............ 514/46
5,736,554 A * 4/1998 Spada et al. ............ 514/303

\* cited by examiner

*Primary Examiner*—Louise N. Leary
(74) *Attorney, Agent, or Firm*—Roberts Abokhair & Mardula, LLC

(57) ABSTRACT

The present invention discloses a method for measuring myocardial function in a mammal in need of such measurement by: a) administering 2-substituted adenosine carboxamide derivatives at a dosage rate of less than 1 μg/kg/min, preferably between about 0.01 and 1 μg/kg/min; and then: b) performing a technique on the mammal to detect myocardial function. The method can be used to diagnose myocardial dysfunction by electrophysiologic analysis or by imaging the vasculature of the heart, especially under conditions that simulate stress.

12 Claims, No Drawings

DIAGNOSTIC USES OF 2-SUBSTITUTED ADENOSINE CARBOXAMIDES

FIELD OF THE INVENTION

The present invention relates to the use of 2-substituted adenosine carboxamide derivatives in the diagnosis of myocardial dysfunction by electrophysiologic analysis or by imaging the vasculature of the heart, especially under conditions that simulate stress.

BACKGROUND OF THE INVENTION

Adenosine has been known since the early 1920's to have potent vasodilator activity. It is a local hormone released from most tissues in the body during stress, especially hypoxic and ischemic stress (see Olsson et al., Physiological Reviews, 70(3), 761–845, 1990). As such, adenosine and adenosine-releasing agents are now commonly used to simulate the stress condition for diagnostic purposes (see The Medical Letter, 33(853), 1991).

Thallium-201 myocardial perfusion imaging is currently the most common approach in the use of stress-simulating agents as a means of imaging the coronary vessels to obtain a diagnosis of coronary artery disease. This is effected by injection of the stress agent such as adenesine at a dose of about 1 mg/kg body weight, followed by injection of the radionuclide, thallium-201, and scanning with a rotating gamma counter to image the heart and generate a scintigraph (see McNulty, Cardiovascular Nursing, 28(4), 24–29, 1992).

The mechanism underlying thallium-201 myocardial perfusion imaging is as follows: adenosine acting on coronary adenosine receptors causes relaxation of the coronary arterioles, thereby increasing blood flow throughout the heart. This effect is short-lasting and at a dose of 1 mg/kg, adenosine does not dilate other peripheral blood vessels to produce substantial systemic hypotension. Diseased or otherwise blocked coronary vessels will not further dilate in response to adenosine and the subsequent flow of thallium-201 through the heart will be less in these regions of hypoperfusion relative to other more normal areas of the heart. The resulting image allows the diagnostitian to quantitate the amount and severity of the coronary perfusion defect. This analysis is of paramount importance in selecting any further course of therapy and intervention by the physician [See U.S. Pat. No. 5,070,877 (Mohiuddin et al.) and U.S. Pat. No. 4,824,660 (Angello et al.)].

The use of adenosine and like-acting analogs is associated with certain side-effects. Adenosine acts on at least two subclasses of adenosine receptors, $A_1$ or $A_2$, both of which are found in the heart. The $A_1$ receptor subtype, when activated by adenosine, among other actions, slows the frequency and conduction velocity of the electrical activity that initiates the heart beat. Sometimes adenosine, particularly at doses near 1 mg/kg, even blocks (stops) the heart beat during this diagnostic procedure—a highly undesirable action. The $A_2$ receptor subtype is found in blood vessels and is further divided into $A_{2a}$ and $A_{2b}$ receptor subtypes (see Martin et al., Journal of Pharmacology and Experimental Therapeutics, 265(1), 248–253, 1993). It is the $A_{2a}$ receptor that is specifically responsible for mediating coronary vasodilation—the desired action of adenosine in the diagnostic procedure. Thus, the side-effects of adenosine and adenosine releasing agents result substantially from non-selective stimulation of the various adenosine receptor subtypes. Clearly, a better procedure would be to use a substance as a stress agent that selectively activates only the $A_{2a}$ receptor, is short acting and works at doses substantially below 1 mg/kg body weight.

U.S. Pat. No. 5,477,857 to McAfee et al. discloses various diagnostic uses of hydrazinoadenosines. The compounds described in the McAfee patent are extremely effective for perfusion imaging, but suffer from a few limitations. Several of the compounds McAfee discloses as being useful are extremely labile, and prone to hydrolysis in vivo. For this reason, they have extremely short half-lives in vivo, and also must be stored in lyophilized form. Further, it is believed that one of the degradation processes for adenosine derivatives involves de-ribosylation of the derivative to form an adenine derivative, which can potentially be incorporated into genetic material of patients to whom they are administered. When using adenosine derivatives instead of adenosine, it would be advantageous to use compounds which are relatively more hydrophobic, and therefore, less likely to be absorbed by the cells, than adenosine derivatives which are commonly used.

It would be advantageous to provide perfusion imaging methods which overcome these limitations. The present invention provides such methods.

SUMMARY OF THE INVENTION

This invention is directed to the administration of 2-substituted adenosine carboxamide derivatives as a pharmacological stressor in conjunction with any one of several noninvasive diagnostic procedures available. For example, intravenous administration may be used in conjunction with thallium-201 myocardial perfusion imaging to assess the severity of myocardial ischemia.

Any one of several different radiopharmaceuticals may be substituted for thallium-201 (e.g., rubidium-82, technetium 99 m, derivatives of technetium 99 m, nitrogen-13, iodine 123, etc.). Similarly, the 2-substituted adenosine carboxamide derivatives may be administered as a pharmacological stressor in conjunction with radionuclide angiography to assess the severity of myocardial dysfunction. In this case, radionuclide angiographic studies may be first pass or gated equilibrium studies of the right and/or left ventricle. Similarly, the compounds may be administered as a pharmacological stressor in conjunction with echocardiography to assess the presence of regional wall motion abnormalities. Similarly, the 2-substituted adenosine carboxamide derivatives may be administered as a pharmacological stressor in conjunction with invasive measurements of coronary blood flow such as by intracardiac catheter to assess the functional significance of stenotic coronary vessels.

DESCRIPTION OF THE PREFERRED EMBODIMENTS

The methods described herein use specific compounds having activity as $A_2$ adenosine receptor agonists, namely 2-substituted adenosine carboxamide derivatives. The method involves using one or more of the compounds described herein as a substitute for exercise in conjunction with imaging to detect the presence and/or assess the severity of ischemic ventricular dysfunction in humans wherein ischemic ventricular dysfunction is measured by any one of several imaging techniques including echocardiography, contrast ventriculography, or radionuclide angiography.

It is essential that the compounds herein be capable of binding selectively to $A_2$ adenosine receptors, e.g., in a human. Methods for determining whether compounds bind selectively to $A_2$ adenosine receptors, e.g., in a human, are well known to those of skill in the art, and include, for example, competitive binding studies. Suitable competitive binding studies are disclosed in the Examples section.

The following definitions will be useful in understanding the compounds and methods described herein.

Definitions

As used herein, a compound is selective for the $A_2$ receptors if the ratio of $A_2/A_1$ and $A_2/A_3$ activity is greater than about 20, preferably between 50 and 100, and more preferably, greater than about 100.

As used herein, the term "lower" referred to above and hereinafter in connection with organic radicals or compounds respectively defines such with up to and including 7, preferably up to and including 4 and advantageously one or two carbon atoms.

As used herein, the term "alkyl" refers to monovalent straight, branched or cyclic alkyl groups preferably having from 1 to 20 carbon atoms ("alkyl"). A lower alkyl group is straight chain or branched and preferably contains 1 to 4 carbon atoms, and represents for example ethyl, propyl, butyl, and advantageously methyl.

This term is exemplified by groups such as methyl, ethyl, n-propyl, iso-propyl, -butyl, iso-butyl, n-hexyl, and the like. The terms "alkylene" and "lower alkylene" refer to divalent radicals of the corresponding alkane. Further, as used herein, other moieties having names derived from alkanes, such as alkoxyl, alkanoyl, alkenyl, cycloalkenyl, etc. when modified by "lower," have carbon chains of ten or less carbon atoms. In those cases where the minimum number of carbons are greater than one, e.g., alkenyl (minimum of two carbons) and cycloalkyl, (minimum of three carbons), it is to be understood that "lower" means at least the minimum number of carbons.

As used herein, "alkaryl" refers to an alkyl group with an aryl substituent. Binding is through the aryl group. "Aralkyl" refers to an aryl group with an alkyl substituent, where binding is through the alkyl group. These terms are analogously described with respect to aralkoxy and alkaryloxy, and other terms with similar description of linkages between aryl and alkyl groups.

As used herein, the term "alkoxy" refers to the group "alkyl-O-", where alkyl is as defined above. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. A lower alkoxy group is straight chain or branched and preferably contains 1 to 4 carbon atoms, and represents for example methoxy, ethoxy, propoxy.

Lower alkylene is straight chain or branched alkylene and preferably contains 1 to 4 carbon atoms, and represents for example methylene, ethylene.

Lower alkenylene is straight chain or branched alkenylene; preferably contains 2 to 4 carbon atoms and represents for example ethenylene, 1- or 2-propenylene.

Aryl is an optionally substituted carbocyclic or heterocyclic aromatic radical, a carbocyclic aromatic radical being preferably phenyl or 1- or 2-naphthyl each optionally substituted by one to three of lower alkyl, lower alkoxy, hydroxy, halogen or trifluoromethyl, or by a substituent —W—Z in which W represents a direct bond, lower alkylene, thio-lower alkylene or oxy-lower alkylene and Z represents cyano, carboxy or carboxy derivatized in the form of a pharmaceutically acceptable ester or amide; and a heterocyclic aromatic radical being preferably pyridyl or thienyl. Advantageously aryl represents phenyl or phenyl substituted as described above.

Examples of aryl groups include unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can further optionally be substituted with from 1 to 5 substituents and preferably 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, aminoacyl, acyloxy, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, -SO-heteroaryl, —$SO_2$-alkyl, —$SO_2$-substituted alkyl, —SO2-aryl, —$SO_2$-heteroaryl, trihalomethyl. Preferred substituents include alkyl, alkoxy, halo, cyano, nitro, trihalomethyl, and thioalkoxy.

Aryl-lower alkyl represents preferably aryl-$C_1$–$C_4$-alkyl in which aryl represents a carbocyclic or heterocyclic aromatic radical as defined above, e.g. benzyl or 1- or 2-phenyl-(ethyl, propyl or butyl), each unsubstituted or substituted on phenyl ring as defined under aryl above; or 2-, 3- or 4-pyridylmethyl or 2-(2-, 3- or 4-pyridyl)-(ethyl, propyl or butyl); or 1- or 2-naphthylmethyl or 2-(1- or 2-naphthyl)-(ethyl, propyl or butyl).

Aryl-hydroxy-lower alkyl represents preferably aryl-hydroxy-$C_1$–$C_4$-alkyl in which aryl preferably represents a carbocyclic aromatic radical as defined above, e.g. 2-phenyl-2-hydroxy-(ethyl, propyl or butyl).

Diaryl-lower alkyl represents preferably diphenyl-$C_1$–$C_4$-alkyl, e.g. omega-diphenyl- (methyl, ethyl or propyl).

As used herein, the term "cycloalkyl" refers to cyclic alkyl groups of from 3 to 12 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantyl, and the like. Cycloalkyl preferably represents 3 to 6 ring membered cycloalkyl, i.e. $C_3$–$C_6$-cycloalkyl. $C_3$–$C_6$-cycloalkyl represents cyclopropyl, cyclobutyl, cyclopentyl or cyclohexyl, preferably cyclopropyl.

Cycloalkyl-lower alkyl represents preferably (cyclopentyl or cyclohexyl)-$C_1$–$C_4$-alkyl, advantageously 1- or 2-(cyclopentyl or cyclohexyl)-ethyl, propyl or butyl.

Bicycloalkyl represents preferably bicycloheptyl or bicycloheptyl substituted by lower alkyl, particularly unsubstituted or lower alkyl substituted bicyclo[2,2,1]-heptyl, such as bornyl, neobornyl, isobornyl, norbornyl, e.g. 2-norbornyl. The term bornyl is synonymous with bornanyl.

Cycloalkenyl-lower alkyl represents preferably 1-cyclohexenyl-lower alkyl.

As used herein, the term "heteroaryl" refers to an aromatic carbocyclic group of from 1 to 15 carbon atoms and 1 to 4 heteroatoms selected from the group consisting of oxygen, nitrogen and sulfur within at least one ring (if there is more than one ring).

Unless otherwise constrained by the definition for the heteroaryl substituent, such heteroaryl groups can be optionally substituted with from 1 to 5 substituents and preferably 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, aminoacyl, acyloxy, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and trihalomethyl. Preferred substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl).

"Heterocycle" or "heterocyclic" refers to a monovalent saturated or unsaturated group having a single ring or multiple condensed rings, from 1 to 15 carbon atoms and from 1 to 4 hetero atoms selected from the group consisting of nitrogen, sulfur and oxygen within the ring.

Unless otherwise constrained by the definition for the heterocyclic substituent, such heterocyclic groups can be optionally substituted with 1 to 5 substituents selected from the group consisting of alkyl, substituted alkyl, alkoxy, substituted alkoxy, aryl, aryloxy, halo, nitro, heteroaryl, thiol, thioalkoxy, substituted thioalkoxy, thioaryloxy, trihalomethyl, and the like. Such heterocyclic groups can have a single ring or multiple condensed rings.

As to any of the above groups that contain 1 or more substituents, it is understood, of course, that such groups do not contain any substitution or substitution patterns which are sterically impractical and/or synthetically non-feasible.

The term "protecting group" or "blocking group" refers to any group which when bound to one or more hydroxyl, amino or carboxyl groups of the compounds (including intermediates thereof such as the aminolactams, aminolactones, etc.) prevents reactions from occurring at these groups and which protecting group can be removed by conventional chemical or enzymatic steps to reestablish the hydroxyl, amino or carboxyl group. Preferred removable amino blocking groups include conventional substituents such as t-butyoxycarbonyl (t-BOC), benzyloxycarbonyl (CBZ), and the like which can be removed by conventional conditions compatible with the nature of the product.

As used herein, the term "halogen" refers to bromide, chloride, fluoride and iodide radicals.

Halogen is preferably chloro, but may also be fluoro, bromo or iodo.

Tetrahydropyranyl represents preferably 4-tetrahydropyranyl.

Tetrahydrothiopyranyl represents preferably 4-tetrahydrothiopyranyl.

Bicycloalkenyl represents preferably bicycloheptenyl or bicycloheptenyl substituted by lower alkyl, particularly unsubstituted or lower alkyl-substituted bicyclo[2.2.1]heptenyl, such as 5-norbornen-2-yl, or unsubstituted or lower alkyl-substituted bicyclo[3.1.1]heptenyl, such as 6,6-dimethylbicyclo[3.1.1]hept-2-en-2-yl.

Adamantyl represents preferably 1-adamantyl.

Hydroxy-lower alkyl represents preferably 2-, 3- or 4-hydroxy-C$_2$–C$_4$-alkyl, advantageously hydroxyethyl.

Pyridyl represents 2-, 3- or 4-pyridyl, advantageously 2- or 3-pyridyl.

Thienyl represents 2- or 3-thienyl.

Aryl-cycloalkyl represents preferably phenyl-C$_3$–C$_6$-cycloalkyl, for example 2-phenylcyclohexyl or 2-phenylcyclopropyl.

A bicyclic benzo-fused 5- or 6-membered saturated carbocyclic radical, as a substituent R$_1$ depicted by formula B above in which A represents methylene, represents preferably 1,2,3,4-tetrahydro-2-naphthyl or 2-indanyl, each unsubstituted or substituted on benzo portion as indicated above for phenyl under aryl.

A bicyclic benzo-fused 5- or 6-membered saturated heterocyclic radical, as a substituent depicted by formula B above in which A represents oxy or thio, represents preferably 3,4-dihydro-2H-[1]-3-benzopyranyl or 3,4-dihydro-2H-[1]-3-benzothiopyranyl, each unsubstituted or substituted on the benzo portion as indicated above for phenyl under aryl.

A lower alkoxycarbonyl group preferably contains 1–4 carbon atoms in the alkoxy portion and represents for example: methoxycarbonyl, propoxycarbonyl, isopropoxycarbonyl or advantageously ethoxycarbonyl.

Lower alkanoyl represents preferably straight chain or branched C$_1$–C$_4$-alkanoyl, e.g. acetyl, isobutyryl, pivaloyl.

Lower alkoxy-lower alkanoyl represents preferably lower alkoxy-C$_2$–C$_4$-alkanoyl, e.g. methoxyacetyl, 3-ethoxypropionyl.

Aroyl represents preferably benzoyl, benzoyl substituted by one to three of lower alkyl, lower alkoxy, halogen or trifluoromethyl; 2-, 3- or 4-pyridylcarbonyl; or 2- or 3-thienylcarbonyl.

Mono- and di-lower alkylcarbamoyl represents for example N-methyl-, N-ethyl-, N,N-dimethyl- and N,N-diethylcarbamoyl.

Carboxy esterified in the form of a pharmaceutically acceptable ester represents advantageously an ester that may be convertible by solvolysis or under physiological conditions to the free carboxylic acid, e.g. lower alkoxycarbonyl; (amino, mono- or di-lower alkylamino)substituted lower alkoxycarbonyl; carboxy substituted lower alkoxycarbonyl, e.g. alpha-carboxy-substituted lower alkoxycarbonyl; lower alkoxycarbonyl-substituted lower alkoxycarbonyl, e.g. alpha-lower alkoxycarbonyl-substituted lower alkoxycarbonyl; aryl-substituted lower alkoxycarbonyl, e.g. optionally substituted benzyloxy carbonyl or pyridylmethoxycarbonyl; (hydroxy, lower alkanoyloxy or lower alkoxy)-substituted lower alkoxycarbonyl, e.g. pivaloyloxymethoxycarbonyl; (hydroxy, lower alkanoyloxy or lower alkoxy)-substituted lower alkoxymethoxycarbonyl; bicycloalkoxycarbonyl-substituted lower alkoxycarbonyl, e.g. bicyclo[2,2,1]-heptyloxycarbonyl-substituted lower alkoxycarbonyl, especially bicyclo [2,2,1]heptyloxycarbonyl-substituted methoxycarbonyl such as bornyloxycarbonylmethoxycarbonyl; 3-phthalidoxycarbonyl; (lower alkyl, lower alkoxy, halo)-substituted 3-phthalidoxycarbonyl; lower alkoxycarbonyloxy-lower alkoxycarbonyl, e.g. 1-(methoxy- or ethoxycarbonyloxy)-ethoxycarbonyl; aryloxycarbonyl, e.g. phenoxycarbonyl or phenoxycarbonyl advantageously substituted at the ortho position by carboxy or lower alkoxycarbonyl. Preferred are the lower alkyl esters, omega-(di-lower alkylamino)-alkyl esters, e.g. the di-(C$_1$–C$_4$-alkylamino)-ethyl esters, and pivaloyloxymethyl esters.

Carboxy derivatized in the form of a pharmaceutically acceptable amide represents preferably carbamoyl, mono-lower alkylcarbamoyl or di-lower alkylcarbamoyl.

Carboxy derivatized in form of a pharmaceutically acceptable amide further represents C$_1$–C$_2$O-alkylcarbamoyl, di-C$_1$–C$_2$O-alkyl-carbamoyl, aryl-lower alkylcarbamoyl, di-lower alkylamino-lower alkylcarbamoyl, (pyrrolidino, piperidino or morpholino)-lower alkylcarbamoyl, 2-oxopyrrolidino-lower alkylcarbamoyl, morpholinocarbonyl, piperidinocarbonyl unsubstituted or substituted with aryl-lower alkyl, aryl, or lower alkylcarbonyl, or piperazinocarbonyl substituted at the 4-position with aryl-lower alkyl, aryl or lower alkylcarbonyl. Aryl in the above represents preferably phenyl, phenyl substituted by lower alkyl, lower alkoxy, hydroxy, halogen or trifluoromethyl, or heteroaryl such as indolyl (advantageously 3-indolyl) or pyridyl.

The pharmaceutically acceptable ester derivatives in which one or more free hydroxy groups are esterified in the form of a pharmaceutically acceptable ester are particularly prodrug esters that may be convertible by solvolysis under physiological conditions to the compounds of formula I having free hydroxy groups.

Preferred as said prodrug pharmaceutically acceptable esters are straight chain or branched lower alkanoic acid esters, e.g., the acetic, isobutyric, pivaloic acid esters; lower alkoxy-lower alkanoic acid esters, e.g., the methoxyacetic, 3-ethoxypropionic acid esters; arylcarboxylic acid esters, e.g., the benzoic, nicotinic acid esters; carbamic and mono or di-lower alkylcarbamic acid esters (carbamates), e.g. the mono- or di-ethylcarbamic or N-mono- or di-methylcarbamic acid esters. Most preferred are the lower alkanoic acid and lower alkoxyalkanoic acid esters.

Pharmaceutically acceptable salts are generally acid addition salts, which are preferably such of therapeutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid. For compounds having a free carboxy group, pharmaceutically acceptable salts are also derived from bases, e.g. alkali metal salts, such as the sodium salt, or salts derived from pharmaceutically acceptable amines, such as tromethamine.

The following abbreviations are used herein: Abbreviations: [$^{125}$I]AB-MECA, [$^{125}$I]N$^6$-(4-amino-3-iodobenzyl)adenosine-5'N-methyluronamide;(R)-PIA, (R)-N$^6$-(phenylisopropyl)adenosine; DMSO, dimethylsulfoxide; I-AB-MECA, N$^6$-(4-amino-3-iodobenzyl)adenosine-5'-N-methyluronamide; IB-MECA, N$^6$-(3-iodobenzyl)adenosine-5'-N-methyluronamide; Ki, equilibrium inhibition constant; NECA, 5'-N-ethylcarboxamido adenosine; THF, tetrahydrofuran; Tris, tris(hydroxymethyl)aminomethane.

I. The 2-substituted Adenosine Carboxamide Derivatives

The compounds have the following structural formula:
Compounds of the formula I

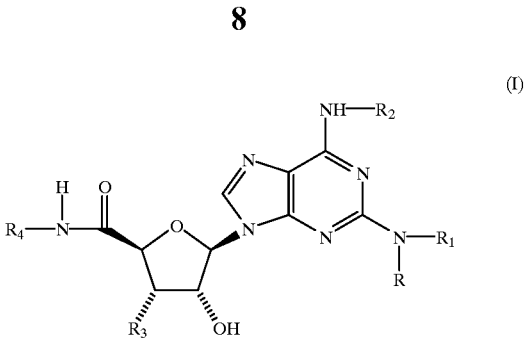

wherein R represents hydrogen or lower alkyl; $R_1$ represents $C_3$–$C_6$-cycloalkyl optionally substituted by lower alkyl, $C_3$–$C_6$-cycloalkyl-lower alkyl optionally substituted by lower alkyl, bicycloalkyl, bicycloalkyl-lower alkyl, aryl, aryl-lower alkyl, aryl-$C_3$–$C_6$-cycloalkyl, 9-fluorenyl, diaryllower alkyl, 9-fluorenyl-lower alkyl, cycloalkenyl-lower alkyl, bicycloalkenyl-lower alkyl, tetrahydropyranyl-lower alkyl, tetrahydrothio-pyranyl-lower alkyl or adamantyllower alkyl: or $R_1$ represents a bicyclic benzo-fused 5- or 6-membered saturated carbocyclic radical or a benzo-fused 5- or 6-membered saturated heterocyclic radical containing a heteroatom selected from oxygen and sulfur which is directly attached to the fused benzene ring, any said bicyclic radical being unsubstituted or substituted on the benzo portion by lower alkyl, lower alkoxy, hydroxy, halogen or trifluoromethyl, or by a substituent —W—Z in which W represents a direct bond, lower alkylene, lower alkenylene, thio-lower alkylene or oxy-lower alkylene and Z represents cyano, carboxy or carboxy derivatized in the form of a pharmaceutically acceptable ester or amide, or $R_1$ represents any said bicyclic radical substituted-lower alkyl; or $R_1$ represents aryl-hydroxy lower alkyl; $R_2$ represents hydrogen, lower alkyl or aryl-lower alkyl; $R_3$ represents hydrogen or hydroxy; $R_4$ represents hydrogen, lower alkyl, aryl-lower alkyl, $C_3$–$C_6$-cycloalkyl or hydroxy-lower alkyl; aryl represents an optionally substituted carbocyclic aromatic radical, being preferably 1- or 2-naphthyl, phenyl, or naphthyl or phenyl substituted by one to three of lower alkyl, lower alkoxy, hydroxy, halogen or trifluoromethyl, or naphthyl or phenyl substituted by a substituent —W—Z in which W represents a direct bond, lower alkylene, lower alkenylene, thio-lower alkylene or oxy-lower alkylene and Z represents cyano, carboxy or carboxy derivatized in the form of a pharmaceutically acceptable ester or amide; or aryl represents a heterocyclic aromatic radical, being preferably pyridyl or thienyl, each optionally substituted as described above for phenyl; pharmaceutically acceptable ester derivatives thereof in which free hydroxy groups are esterified in the form of a pharmaceutically acceptable ester; and pharmaceutically acceptable salts thereof.

Preferred are the compounds of formula I wherein R represents hydrogen or lower alkyl; $R_1$ represents $C_3$–$C_6$-cycloalkyl-lower alkyl; or $R_1$ represents aryl-lower alkyl wherein aryl represents pyridyl, thienyl, naphthyl, phenyl, phenyl substituted by one or two substituents selected from halogen, trifluoromethyl, lower alkoxy, hydroxy and lower alkyl, or phenyl substituted by a substituent —W—Z in which W represents a direct bond, lower alkylene, lower alkenylene, thio-lower alkylene or oxy-lower alkylene, and Z represents cyano, carboxy, carboxy derivatized in the form of a pharmaceutically acceptable ester or carboxy derivatized in the form of a pharmaceutically acceptable amide; or $R_1$ represents a substituent of the formula B

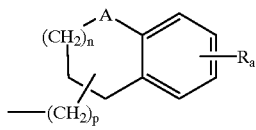

in which A represents methylene, oxy or thio, n represents zero or one, p represents zero, one or two, and $R_a$ represents hydrogen, lower alkyl, lower alkoxy, halogen or —W—Z as defined above; $R_2$ represents hydrogen or lower alkyl; $R_3$ represents hydrogen or hydroxy; $R_4$ represents hydrogen, lower alkyl, $C_3$–$C_6$-cycloalkyl, hydroxy-lower alkyl, or aryl-lower alkyl in which aryl represents pyridyl, thienyl or phenyl; pharmaceutically acceptable ester derivatives thereof in which one or more free hydroxy groups are esterified in the form of a pharmaceutically acceptable ester; and pharmaceutically acceptable salts thereof.

Preferred are the compounds of formula (Ia)

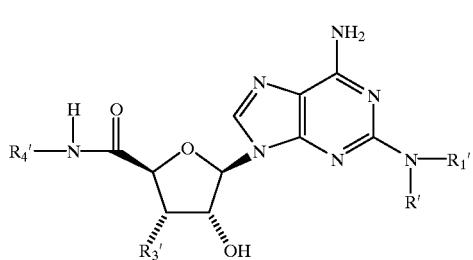

wherein R' represents hydrogen or lower alkyl; $R_1$' represents $C_3$–$C_6$-cycloalkyl-lower alkyl; or $R_1$' represents aryl-lower alkyl in which aryl represents thienyl, pyridyl, phenyl or phenyl monosubstituted by halogen, trifluoromethyl, lower alkoxy, hydroxy, lower alkyl, or by a substituent —W—Z in which W represents a direct bond, lower alkylene, thio-lower alkylene or oxy-lower alkylene, and Z represents cyano, carboxy, lower alkoxycarbonyl, carbamoyl, N-mono- or N,N-di-lower alkylcarbamoyl; or R1' represents a substituent of the formula B'

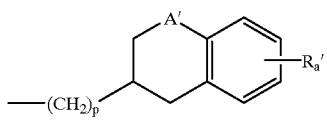

in which A' represents a direct bond, methylene, oxy or thio, p represents zero, one or two and $R_a$' represents hydrogen, lower alkyl, lower alkoxy, hydroxy, halogen or —W—Z as defined above; or $R_1$' represents aryl-hydroxy-lower alkyl in which aryl has meaning as defined above; $R_3$' represents hydrogen or hydroxy; and $R_4$' represents hydrogen, lower alkyl, $C_3$–$C_6$-cycloalkyl or hydroxy-lower alkyl; pharmaceutically acceptable prodrug ester derivatives thereof in which one or more free hydroxy groups are esterified in the form of a pharmaceutically acceptable ester; and pharmaceutically acceptable salts thereof.

Preferred are the said compounds of formula I and Ia wherein $R_3$ and $R_3$', respectively, represent hydroxy, and ester derivatives thereof.

Particularly preferred are the compounds of formula Ia above wherein $R_3$' represents hydroxy; $R_4$' represents lower alkyl, cyclopropyl or hydroxy-lower alkyl; and R', $R_1$', A', p and $R_a$ ' have meaning as defined above; pharmaceutically acceptable prodrug ester derivatives thereof in which free hydroxy groups are esterified in the form of a pharmaceutically acceptable ester; and pharmaceutically acceptable salts thereof.

Further preferred are the compounds of formula II

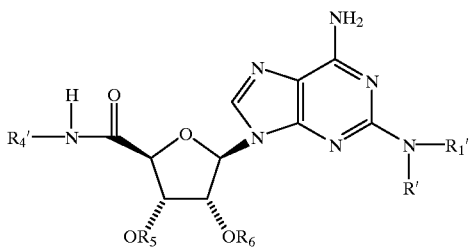

wherein R' represents hydrogen or $C_1$–$C_4$-alkyl; $R_1$' represents ($C_5$–or $C_6$)-cycloalkyl-$C_1$–$C_4$-alkyl, or $R_1$' represents aryl-$C_1$–$C_4$-alkyl in which aryl represents 2- or 3-thienyl, 2-, 3- or 4-pyridyl, phenyl, or phenyl monosubstituted by halogen, trifluoromethyl, lower alkoxy, lower alkyl or by a substituent —W—Z in which W represents a direct bond, $C_1$–$C_4$-alkylene, thio-$C_1$–$C_3$-alkylene or oxy-$C_1$–$C_3$-alkylene and Z represents cyano, carboxy, lower alkoxycarbonyl, carbamoyl, N-mono- or N,N-di-lower alkylcarbamoyl; or $R_1$' represents aryl-hydroxy-$C_1$–$C_4$-alkyl in which aryl has meaning as defined above; $R_4$' represents $C_1$–$C_4$-alkyl, cyclopropyl or hydroxy-$C_2$–$C_4$-alkyl; $R_5$ and $R_6$ represent hydrogen, lower alkanoyl, lower alkoxy-lower alkanoyl, aroyl, carbamoyl, mono- or di-lower alkylcarbamoyl; and pharmaceutically acceptable salts thereof.

Particular preferred are said compounds of formula II wherein R' represents $C_1$–$C_3$-alkyl or hydrogen; $R_1$' represents $CH_2$ $CH_2$-(cyclohexyl or cyclopentyl); or $R_1$' represents —$CH_2$ $CH_2$-aryl in which aryl represents 2- or 3-pyridyl, phenyl, or phenyl monosubstituted by a substituent —$CH_2$ $CH_2$ —Z or —$OCH_2$—Z in which Z represents cyano, carboxy, lower alkoxycarbonyl, carbamoyl, N-mono- or N,N-di-lower alkylcarbamoyl; $R_4$' represents ethyl or hydroxyethyl; $R_5$ and $R_6$ represent hydrogen, lower alkanoyl or lower alkoxy-$C_2$–$C_4$-alkanoyl; and pharmaceutically acceptable salts thereof.

Most preferred are the compounds of formula II wherein R' represents hydrogen or methyl; $R_1$' represents cyclohexylethyl; or $R_1$' represents 2-phenylethyl, 2-(2-pyridyl)-ethyl or 2-phenylethyl substituted in the para position by $CH_2$ $CH_2$ Z in which Z represents carboxy, lower alkoxycarbonyl, carbamoyl or mono-lower alkylcarbamoyl: $R_4$' represents ethyl: $R_5$ and R6 represent hydrogen; and pharmaceutically acceptable salts thereof.

A particular preferred embodiment of the invention is also represented by the compounds of formula IIa

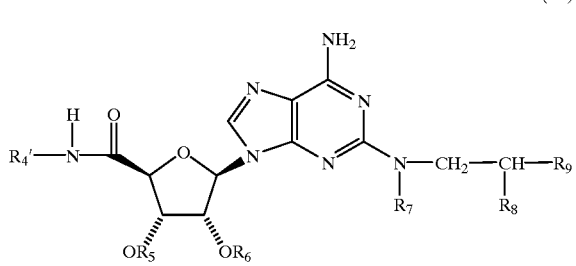

(IIa)

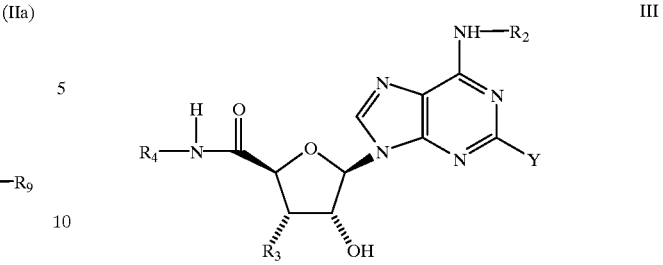

III wherein $R_4'$ represents ethyl; $R_5$ and $R6$ represent hydrogen or lower alkanoyl; $R_7$ represents hydrogen or methyl; $R_8$ represents hydrogen or methyl; $R_9$ represents cyclohexyl, phenyl, or phenyl monosubstituted by halogen, trifluoromethyl, lower alkyl, lower alkoxy or —$CH_2$ $CH_2$—Z in which Z represents carboxy or lower alkoxycarbonyl; and pharmaceutically acceptable salts thereof.

The compounds of formula II and IIa as defined above are the most selective adenosine-2 receptor agonists and accordingly are preferred compounds for use in the methods described herein. Particular preferred compounds include those where, in formula I, R represents hydrogen, in formula Ia, R' represents hydrogen, in formula II, R' represents hydrogen and in formula IIa, $R_7$ represents hydrogen. These are particularly preferred compounds because of their high affinity and selectivity for $A_2$ adenosine receptors. The compound described in Example 2 g is about 100 fold more selective for the A-2 than for the A-1 receptor in vitro. The currently preferred compound is CGS-21680 ((2-p-carboxyethyl)phenylamino-5'-N-carboxamidoadenosine).

II. Compound Preparation

Those skilled in the art of organic chemistry will appreciate that reactive and fragile functional groups often must be protected prior to a particular reaction, or sequence of reactions, and then restored to their original forms after the last reaction is completed. Usually groups are protected by converting them to a relatively stable derivative. For example, a hydroxyl group may be converted to an ether group and an amine group converted to an amide or carbamate. Methods of protecting and de-protecting, also known as "blocking" and "de-blocking," are well known and widely practiced in the art, e.g., see T. Green, *Protective Groups in Organic Synthesis*, John Wiley, New York (1981) or *Protective Groups in Organic Chemistry*, Ed. J. F. W. McOmie, Plenum Press, London (1973).

The general method for preparing the above compounds involves

The compounds of the invention, i.e. of formula I and herein cited derivatives thereof, are preferably prepared by process (a) which comprises condensing a compound of the formula wherein $R_2$, $R_3$ and $R_4$ have meaning as defined above and Y represents a leaving group, with a compound of the formula $R_1$—NH—R    IV wherein R and $R_1$ have meaning as defined above; and, as required, temporarily protecting any interfering reactive group(s) in the starting materials and then subsequently removing the protecting groups to yield a resulting compound of formula I; and, if desired, converting a resulting compound of formula I into another of the invention, and if desired, converting a resulting free compound into a salt or a resulting salt into a free compound or into another salt, and if required, separating any mixture of isomers or racemates obtained into the single isomers or racemates, and if required, resolving a racemate into the optical antipodes.

The compounds described herein may also be prepared by process (b) which comprises condensing a compound of the formula

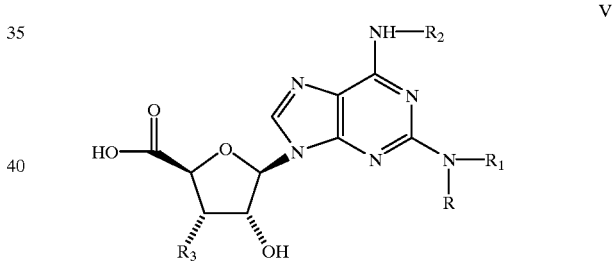

V wherein $R_1$, $R_2$ and $R_3$ have meaning as defined above, or a reactive functional derivative thereof, with an amine of the formula VI $R_4$—$NH_2$    VI wherein $R_4$ has meaning as defined above; and, as required, temporarily protecting any interfering reactive group(s) in the starting materials and then subsequently removing the protecting groups to yield a resulting compound of formula I; and, if desired, converting a resulting compound of formula I into another of the invention, and if desired, converting a resulting free compound into a salt or a resulting salt into a free compound or into another salt, and if required, separating any mixture of isomers or racemates obtained into the single isomers or racemates, and if required, resolving a racemate into the optical antipodes.

A leaving group in the above processes represents especially halo, for example chloro, bromo or iodo, aliphatically or aromatically substituted sulfonyloxy, for example methylsulfonyloxy or 4-methylphenylsulfonyloxy (tosyloxy), or aliphatically substituted thio, for example lower alkylthio such as methylthio.

In the processes cited herein, reactive functional derivatives of carboxylic acids represent, for example, anhydrides especially mixed anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters are for example succinimido, phthalimido or 4-nitrophenyl esters; lower alkyl esters are for example the methyl or ethyl esters.

In starting compounds and intermediates which are converted to the compounds of the invention in a manner described herein, functional groups present, such as amino and hydroxy, are optionally protected by conventional protecting groups that are common in preparative organic chemistry. Protected amino and hydroxy groups are those that can be converted under mild conditions into free amino and hydroxy groups without the molecular framework being destroyed or undesired side reactions taking place.

Well-known protecting groups that meet these conditions and their introduction and removal are described, for example, in J. F. W. McOmie, "Protective Groups in Organic Chemistry", Plenum Press, London, New York 1973, T. W. Greene, and "Protective Groups in Organic Synthesis", Wiley, New York 1984.

For example, a hydroxy group may be protected in the form of esters, e.g. as acyl derivatives such as the lower alkanoyl, benzoyl, benzyloxycarbonyl or lower alkoxycarbonyl esters, or such hydroxy group may be protected in the form of ethers, e.g. as the lower alkyl 1,2-tetrahydropyranyl, trityl or benzyl ethers.

Hydroxy groups on adjacent carbon atoms can also be protected e.g. in the form of ketals or acetals, such as lower alkylidene e.g. isopropylidene, benzylidene or 5- or 6-membered cycloalkylidene e.g. cyclopentylidene or cyclohexylidene derivatives.

In a resulting protected compound of formula I or intermediate, in which one or more of the functional groups are protected, the protected functional groups, e.g. hydroxy groups, can be liberated in a manner known per se, e.g. by means of solvolysis, especially hydrolysis with acid, or by hydrogenolysis.

The preparation of the compounds of the invention according to process a) which involves the displacement of a leaving group Y (e.g. chloro) in a compound of the formula III or a protected derivative by an amine of the formula IV is preferably carried out at elevated temperature, e.g. at a temperature ranging from about 75° to 150°C., with an excess of the amine, in the absence or presence of a solvent, particularly a polar solvent such as dimethylformamide, or under elevated pressure, or in the presence of a base such as triethylamine or potassium carbonate.

The starting materials of formula III can be prepared by condensing a compound of the formula VII

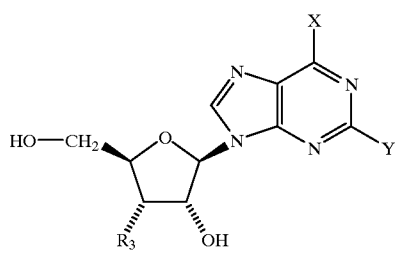

VII or a compound of formula VII in partially protected form, wherein X and Y represent a leaving group, and $R_3$ has meaning as defined above, with a compound of the formula VIII $$R_2-NH_2 \qquad \text{VIII}$$

wherein $R_2$ has meaning as defined above; oxidizing the primary alcohol group in a resulting compound of formula IX

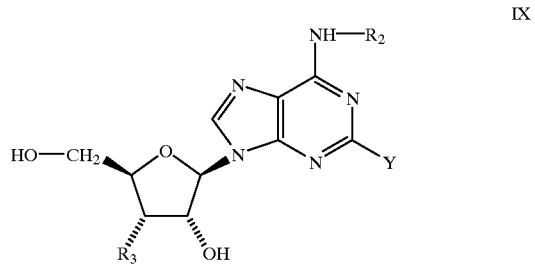

IX in which any secondary hydroxy groups are in protected form, and wherein Y, $R_2$ and $R_3$ have meaning as defined above, to the corresponding carboxylic acid; and converting said carboxylic acid to a corresponding amide of formula III.

The intermediates of formula VII, and protected derivatives thereof, e.g. in which X and Y represent halogen, particularly chloro, are known or are prepared according to methods known in the art relating to N-(.beta.-D-ribofuranosyl)-purine derivatives, for example as described in Chem. Pharm. Bull. 23, 758 (1975).

The displacement of the leaving group X in a compound of formula VII with an amine of formula VIII is carried out essentially as described above for process (a), preferably using about one mole equivalent of the amine, so as to minimize the displacement of the less reactive leaving group Y.

The oxidation of the resulting e.g. 2-halo substituted adenosine derivatives, in which secondary hydroxy groups are in protected form, is carried out for example with potassium permanganate as described in U.S. Pat. No. 4,167,565.

The resulting carboxylic acid is then first converted to a reactive derivative thereof, e.g. the acid chloride, which is condensed with an amine of the formula VI under condition well-known in the art, e.g. as described in U.S. Pat. No. 4,167,565.

The starting materials of formula IV, VI and VIII are either known in the art, or are prepared using methods known in the art, and as described herein.

The preparation of the compounds of the invention according to process (b) involving the conversion of an acid of formula V to a compound of formula I can be carried out using methodology as described above.

The compounds of the invention or intermediates leading thereto can be converted into other compounds of the invention or corresponding intermediates using chemical methodology known in the art and as illustrated herein.

The conversion of compounds of formula I containing free hydroxy groups to ester derivatives thereof may be carried out by condensation with a corresponding carboxylic acid, advantageously as a reactive functional derivative thereof, according to acylation (esterification) procedures well-known in the art.

A compound of the invention with both 2' and 3'-hydroxy groups, e.g. a compound of formula I or Ia wherein $R_3$ or $R_3'$ represents hydroxy and wherein both of the adjacent 2'- and 3'-hydroxy groups are protected in the form of ether, acetal or ketal derivatives as described above, e.g. as the isopropylidene (acetonide) derivative, can be converted to a compound of formula I or Ia wherein $R_3$ or $R_3'$ represents hydrogen by elimination of the 3'-substituent by treatment with a strong base, e.g. sodium hydride in anhydrous isopropanol (sodium isopropoxide) to first yield compound with a double bond between the 3'-4'-carbon atoms, said double bond being subsequently reduced, e.g. by catalytic hydrogenation.

The conversion of the compounds of formula I into pharmaceutically acceptable esters, wherein the 2'-hydroxy group (and 3'-hydroxy group if present) is esterified, can be carried out by condensation with a corresponding carboxylic acid or reactive derivative thereof, according esterification procedures known in the art relating to nucleoside chemistry. For example, an appropriate carboxylic acid anhydride such as acetic anhydride is condensed with a compound of formula I in the presence of asuitable base, e.g. pyridine, triethylamine, 4-(dimethyl-amino)-pyridine, in an inert solvent such as acetonitrile.

A compound of formula I containing a primary amino group (e.g. wherein $NRR_1$ or $NHR_2=NH_2$) may be converted to a compound of formula I wherein $NRR_1$ or NHR2 represents a secondary amino group, e.g. wherein $R_1$ or $R_2$ represents e.g. aryl-lower alkyl, by treatment with a reactive derivative of the alcohol corresponding to $R_1$ or $R_2$, e.g. with an aryl-lower alkyl halide such as an aryl-lower alkyl iodide, according to methodology well-known in the art for alkylation of amines. Similarly, a secondary amine wherein R represents hydrogen may be converted to a tertiary amine wherein R represents lower alkyl.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably near the boiling point for the solvents used, and at atmospheric or superatmospheric pressure.

The invention further includes any variant of the present processes, in which an intermediate product obtainable at any stage thereof is used as starting material and the remaining steps are carried out, or in which the starting materials are formed under the reaction conditions, or in which the reaction components are used in the form of their salts or optically pure antipodes. Whenever desirable, the above processes are carried out after first suitably protecting any potentially interfering reactive functional groups, as illustrated herein.

Advantageously, those starting materials should be used in said reactions that lead to the formation of those compounds indicated above as being preferred.

In case diastereomeric mixtures of the above compounds or intermediates are obtained, these can be separated into the single racemic or optically active isomers by methods in themselves known, e.g. by fractional distillation, crystallization or chromatography.

Any racemic products of formula I or basic intermediates can be resolved into the optical antipodes, for example, by separation of diastereomeric salts thereof, e.g., by the fractional crystallization of d- or 1-(tartrate, dibenzoyltartrate, mandelate or camphorsulfonate) salts.

The compounds can be isolated and used in the free form, or as a pharmaceutically acceptable salt. For example, any resulting free base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide, or any basic salt, e.g., an alkali metal hydroxide or carbonate, or a cation exchange preparation. These or other salts, for example, the picrates, can also be used for purification of the bases obtained; the bases are then first converted into salts. In view of the close relationship between the free compounds and the compounds in the form of their salts, whenever a compound is referred to in this context, a corresponding salt is also intended, provided such is possible or appropriate under the circumstances.

The compounds, including their salts, may also be obtained in the form of their hydrates, or include other solvents used for the crystallization.

III. Formulations

The compounds described above are preferably administered in a formulation including an active compound, i.e., a 2-substituted adenosine carboxamide derivative, together with an acceptable carrier for the mode of administration. Suitable pharmaceutically acceptable carriers are known to those of skill in the art.

The carrier must be pharmaceutically acceptable in the sense of being compatible with the other ingredients of the formulation and not deleterious to the recipient thereof.

The formulations can include carriers suitable for oral, rectal, topical or parenteral (including subcutaneous, intramuscular and intravenous) administration. Preferred carriers are those suitable for oral or parenteral administration.

Formulations suitable for parenteral administration conveniently include sterile aqueous preparation of the active compound which is preferably isotonic with the blood of the recipient. Thus, such formulations may conveniently contain distilled water, 5% dextrose in distilled water or saline. Useful formulations also include concentrated solutions or solids containing the compounds described herein which upon dilution with an appropriate solvent give a solution suitable for parental administration above.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," *Drug Carriers in Biology and Medicine*, pp. 287–341 (Academic Press, 1979). Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925, 673 and 3,625,214, the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into a desired unit dosage form.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

IV. Methods of Use

The method described herein involve administering 2-substituted adenosine carboxamide derivatives as a pharmacological stressor in conjunction with any one of several noninvasive diagnostic procedures available. For example, intravenous administration may be used in conjunction with thallium-201 myocardial perfusion imaging to assess the severity of myocardial ischemia. Any one of several different radiopharmaceuticals may be substituted for thallium-201 (e.g., rubidium-82, technetium 99 m, derivatives of technetium 99 m, nitrogen- 13, iodine 123, etc.).

In another embodiment, the 2-substituted adenosine carboxamide derivatives may be administered as a pharmacological stressor in conjunction with radionuclide angiography to assess the severity of myocardial dysfunction. In this case, radionuclide angiographic studies may be first pass or gated equilibrium studies of the right and/or left ventricle.

In yet another embodiment, the compounds may be administered as a pharmacological stressor in conjunction with echocardiography to assess the presence of regional wall motion abnormalities.

In still another embodiment, the 2-substituted adenosine carboxamide derivatives may be administered as a pharmacological stressor in conjunction with invasive measurements of coronary blood flow such as by intracardiac catheter to assess the functional significance of stenotic coronary vessels.

Myocardial function can be measured by infusing into a mammal in need of such infusion from about 0.001 to about 1 $\mu$g/kg/min of one or more of the compounds described herein. Preferably from about 0.01 to about 1 $\mu$g/kg/min is infused, most preferably from about 0.1 to about 1 $\mu$g/kg/min.

Various modes of administration are contemplated. These modes include administration in a parenteral dosage form, a sublingual or buccal dosage form, a rectal administration form, or administration by a transdermal device at a rate sufficient to cause vasodilation.

These compounds are used with diagnostic techniques to determine myocardial function. For example, the compounds are useful to image and analyze the vascular capacity of any tissue bed. These compounds can also be used in conjunction with any technique designed to image the heart for the purposes of determining coronary reserve capacity and detecting evidence of coronary heart disease.

This method is also useful to replace adenosine or dipyridamole as pharmacological stressors in thallium-201 scintigraphic diagnosis of coronary function and heart disease. Further, these compounds are useful in imaging any vascular bed and, thus, the vascular function of any organ (eg. heart, brain, kidney, muscle, liver, fetus), in conjunction with any method capable of measuring function in that organ, such as scintigraphy, ultrasound, x-ray, laser, etc.

Typical of the imaging techniques used in practicing the method of the present invention are radiopharmaceutical myocardial perfusion imaging planar (conventional scintigraphy, single photon emission computed tomography (SPECT), position emission tomography (PET), nuclear magnetic resonance (NMR), perfusion contrast echocardiography, digital subtraction angiography (DSA) and ultrafast x-ray computed tomography (CINECT). Performance of these techniques is well known to those of skill in the art.

Typically, the methods involve the intravenous infusion of vasodilatory doses of the compounds (0.0001–1 $\mu$g/kg/min) over a short period, followed by the infusion of an imaging agent (e.g., thallium-201), followed by a procedure to detect, record and analyze the image (rotating gamma scintillation analyzer). These dosages are significantly lower than those used when adenosine is administered. There are at least two reasons why this is possible. First, the compounds have significantly longer half-lives than adenosine, and are therefore maintain higher plasma levels. Second, the compounds have significantly higher affinity for the adenosine $A_2$ receptors than adenosine, and therefore, lower concentrations of the compounds are required to achieve the same effect. A further advantage is that the compounds have a lower side effect profile than adenosine due to the high affinity for the adenosine $A_2$ receptors.

The 2-substituted adenosine carboxamide derivatives are also relatively hydrophobic, and should they decompose by way of deribosylation, the resulting adenine derivatives should be less likely to be incorporated into the patient's genetic material than more hydrophilic derivatives.

The methods described herein will be better understood with reference to the following non-limiting examples:

PREPARATIVE EXAMPLES

Details of the synthesis, together with modifications and variations specifically tailored for particular compounds, are set out more fully in the specific examples which follow.

The synthetic examples are also described in U.S. Pat. No. 4,968,697 to Hutchinson et al., the contents of which are hereby incorporated by reference.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by analytical methods, e.g. microanalysis and spectroscopic characteristics (e.g. MS, IR, NMR).

The numbering of the positions of the adenine or purine ring system 10 is as conventionally used in the art (e.g. Merck Index, tenth edition).

EXAMPLE 1

Preparation of 2-(2-phenethylamino)-adenosine-5'-(N-ethyl)-carboxamide

A mixture of 1.15 g of 2-(2-phenethylamino)-2',3'-0-isopropylidene-adenosine-5'-(N-ethyl)-carboxamide and 25 ml of 1N hydrochloric acid is heated at 65° for 1 hour The reaction mixture is neutralized and the product is extracted with ethyl acetate. After drying over MgSO$_4$, the solvent is removed in vacuo and the residue is triturated with ether to afford 2-(2-phenethylamino)-adenosine-5'-(N-ethyl)-carboxamide, m.p. 115°–118°.

The starting material is prepared as follows:

A mixture of 1.04 g of 2-chloro-2',3'-O-isopropylidene-adenosine-5'-(N-ethyl)-carboxamide (U.S. Pat. No. 4,167,565) and 8 g of 2-phenethylamine is heated at 130° for 2 hours. After cooling the excess 2-phenethylamine is removed in vacuo and the residue is chromatographed on silica gel with 5% methanol in methylene chloride as the eluent to afford 2-(2-phenethylamino)-2',3'-O-isopropylidene-adenosine-5'-(N-ethyl)-carboxamide.

EXAMPLE 2

Preparation of Various Adenosine 5'-carboxamides Prepared in a similar manner are:

(a) 2-(2-phenethylamino)-adenosine-5'-(N-cyclopropyl) carboxamide, m.p. 115°–118°;

(b) 2-(p-methoxy-2-phenethylamino)-adenosine-5'-(N-ethyl)-carboxamide, m.p. 110°–115°;

(c) 2-(p-chloro-2-phenethylamino)-adenosine-5'-(N-ethyl)-carboxamide, m.p. 110°–115°;

(d) 2-(2-phenethylamino)-adenosine-5'-(N-methyl) carboxamide, m.p. 188°–190°;

(e) 2-(2-phenethylamino)-adenosine-5'-(N-2-hydroxy-ethyl)-carboxamide, m.p. 157°–160°;

(f) 2(p-fluoro-2-phenethylamino)-adenosine-5'-(N-ethyl)-carboxamide, m.p. 108°–112°;

(g) 2-[p-(2-carboxyethyl)-2-phenethylamino]-adenosine5'-(N-ethyl)-carboxamide, m.p. 197°–202°; hydrochloride salt, m.p. 200°–203°; tromethamine salt, m.p. 100°; sodium salt, m.p. 160°–165°.

The amine starting material is prepared as follows:

A mixture of 5 g of p-bromophenylacetonitrile, 4.6 ml of t-butyl acrylate, 57 mg of palladium diacetate, 310 mg of tri-o-tolylphosphine and 12 ml of triethylamine is refluxed for 5 hours. The reaction mixture is diluted with ethyl acetate and washed with 10% HCl and saturated sodium bicarbonate solution. After drying over magnesium sulfate the solvent is removed in vacuo to yield t-butyl p-(cyanomethyl)-phenylacrylate. This material is dissolved in ethanol and hydrogenated over 1.1 g of 10% palladium on carbon catalyst for 3 days at 3 atmospheres pressure of hydrogen. After filtration the solvent is removed in vacuo and the residue is chromatagraphed on silica gel with ether/hexane (1:1) as the eluent to afford p-(2-t-butoxycarbonyl-ethyl)-phenyl-acetonitrile; 2.8 g of this material is dissolved in 90 ml of tetrahydrofuran and 50 ml of methanol and to this is added 6.2 g of cobalt chloride in 90 ml of water followed by 2.1 g of sodium borohydride in small portions. After filtration and removal of solvent, the residue is chromatagraphed on silica gel with 7.5% ammonia saturated methanol in methylene chloride as the eluent to afford p-(2-t-butoxy-carbonyl-ethyl)-2-phenethylamine as an oil.

(h) 2-p-(2-carboxyethenyl)-2-phenethylamino]-adenosine-5'-(N-ethyl)-carboxamide hydrochloride, m.p. 178°–181°.

The starting material is prepared by reduction of t-butyl p-(cyanomethyl)-phenylacrylate (as obtained in example 2 g) to p-t-butoxycarbonyl-ethenyl)-2-phenethylamine with sodium borohydride and cobalt chloride as described under g) above.

(i) 2-[p-(carboxymethoxy)-2-phenethylamino]-adenosine-5'-(N-ethyl)-carboxamide hydrochloride, m.p. 137°141 °;

The amine starting material is prepared as follows:

A mixture of 3 g of p-hydroxyphenylacetonitrile, 3.6 ml of t-butyl bromoacetate, 6.5 g of potassium carbonate in 45 ml of dimethylformamide is stirred at room temperature for 16 hours. After dilution with water the product is extracted with ether. The ethyl layer is washed with 1N sodium hydroxide, dried over magnesium sulfate and the solvent removed in vacuo to yield p-(t-butoxycarbonylmethoxy)-phenylacetonitrile which is reduced to p-(t-butoxycarbonylmethoxy)-2-phenethylamine with sodium borohydride/cobalt chloride as described for the starting material under (g).

(j) 2-(S-2-phenylpropylamino)-adenosine-5'-(N-ethyl) carboxamide, m.p. 117–121°, prepared from the levorotatory (S)-2-phenylpropylamine, J. Med. Chem. 17, 717 (1974);

(k) 2-(N-methyl-2-phenethylamino)-adenosine-5'-(N-ethyl)-carboxamide, hydrochloride, m.p. 115°–119°, prepared from N-methylphenethylamine;

(l) 2-(p-carboxymethyl-2-phenethylamino)-adenosine-5'-(N-ethyl)-carboxamide hydrochloride, m.p. 140°–145°.

The amine starting material for compound (l) is prepared as follows:

A mixture of 20 g of p-bromophenylacetic acid, 30 ml of ether, 1 ml of sulfuric acid and 35 ml of isobutylene is shaken in a sealed bottle for 24 hours. The reaction mixture is diluted with ether and washed with sodium hydroxide solution. After drying over magnesium sulfate the ether is removed in vacuo to afford the t-butyl ester as an oil. A mixture of 9.6 g of this material is refluxed with a mixture of 6.1 g of N-vinylphthalimide, 160 mg of palladium acetate, 800 mg of tri-o-tolylphosphine, 10 ml of acetonitrile and 8 ml diisopropylethylamine for 24 hours. The reaction is diluted with water, the resulting precipitate is collected and recrystallized from methanol/methylene chloride. The resulting solid is hydrogenated at 4 atmospheres pressure over 2 g of 10% palladium on carbon catalyst in 100 ml of ethanol and 100 ml of tetrahydrofuran for 16 hours at room temperature. After removal of the solvent in vacuo the residue is heated at reflux with 10 ml of hydrazine hydrate and 20 ml of ethanol for 2 hours. The reaction is diluted with ether and washed with 5% potassium hydroxide solution. The ether is dried over magnesium sulfate solution and the solvent is removed in vacuo. The residue is chromatographed on silica gel, with 5% ammonia saturated methanol in methylene chloride as the eluent, to afford p-(t-butoxycarbonylmethyl)-2-phenethylamine as an oil.

(m) 2-[p-(dimethylaminocarbonylmethyl)-2-phenethylamino]-adenosine-5'-(N-ethyl )-carboxamide.

The amine starting material is prepared as follows:

A mixture of 6 g of p-bromophenylacetic acid in 100 ml of methylene chloride and 5 ml of oxalyl chloride is stirred at room temperature for 16 hours. After removal of the solvent in vacuo the residue is dissolved in methylene chloride and treated with excess dimethylamine at room temperature. After 1 hour the reaction mixture is washed with water, the organic layer is dried over magnesium sulfate and the solvent is removed in vacuo to afford p-bromo-N,N-dimethyl-phenylacetamide as an oil, which is converted to p-(dimethylaminocarbonylmethyl)-2-phenethylamine as described for the starting material under 1).

(n) 2-(2-cyclohexylethylamino)-adenosine-5'-(N-ethyl) carboxamide hydrochloride, m.p. 154°–157°;

(o) 2-(2-cyclopentylethylamino)-adenosine-5'-(N-ethyl)-carboxamide;

(p) 2-(N-methyl-2-cyclohexylethylamino)-adenosine-5'-(N-ethyl)-carboxamide;

(q) 2-(p-carboxy-2-phenethylamino)-adenosine-5'-(N-ethyl)-carboxamide. The amine starting material is prepared using methodology under (1) from p-bromobenzoic acid.

EXAMPLE 3

The following compounds of formula Ia wherein $R_3'$ represents hydroxy can be prepared substantially according to the procedures previously described herein.

| | Compound NR'$R_1'$ | $R_4'$ |
|---|---|---|
| (a) | 3,4-dihydro-5-methoxy-2H-[1]-benzothio-pyran-3-ylamino | $CH_2CH_3$ |
| (b) | 2-indanylamino | $CH_2CH_3$ |
| (c) | 1,2,3,4-tetrahydro-2-naphthylamino | $CH_2CH_3$ |
| (d) | 3,4-dihydro-2H-[1]-benzopyran-3-ylamino | $CH_2CH_3$ |
| (e) | NH—$CH_2CH_2$-p-$C_6H_4$—$OCH_2CON(C_2H_5)_2$ | $CH_2CH_3$ |
| (f) | 2,2-diphenylethylamino | $CH_2CH_3$ |
| (g) | 2-(2-pyridyl)-ethylamino | $CH_2CH_3$ |
| (h) | 2-(2-thienyl)-ethylamino | $CH_2CH_3$ |
| (i) | 9-9H-fluorenyl)-methylamino | $CH_2CH_3$ |
| (j) | N-methyl-2-(2-pyridyl)-ethylamino | $CH_2CH_3$ |
| (k) | N-methyl-2-(2-thienyl)-ethylamino | $CH_2CH_3$ |
| (l) | 2-(2-pyridyl)-propylamino | $CH_2CH_3$ |

The starting material for compound (a) is prepared as follows: To a cooled mixture of 30.6 g of m-methoxybenzenethiol, 54.4 g of 45% potassium hydroxide in 100 ml of dimethsulfoxide is added 36.0 g of alipha-(bromomethyl)acrylic acid in 25 ml of dimethylsulfoxide at such a rate as to maintain the reaction temperature at 50°–55°. After 1 hour the reaction mixture is diluted with water and washed with ether. After acidification, the product is extracted with ether, the organic layer is dried over magnesium sulfate and the solvent is removed in vacuo to afford alpha-(3-methoxybenzenethiomethyl)acrylic acid. This material is dissolved in 570 ml of o-dichlorobenzene and 7.2 g of triethylamine and heated to 200° for 5 hours. After cooling, the products are extracted with sodium bicarbonate solution, the aqueous layer is acidified and the products extracted with ether. After drying over magnesium sulfate, the solvent is removed in vacuo to afford a mixture of 3,4-dihydro-5-methoxy-2-H[1]-benzothiopyran-3-carboxylic acid and 3,4-dihydro-7-methoxy-2H-[1]-benzothiopyran-3-carboxylic acid.

This mixture of acids is dissolved in 500 ml of t-butyl alcohol and treated with 17 g of triethylamine and 36 ml of diphenylphosphoryl azide. After 5 hours reflux, the solvent is removed in vacuo and the residue is dissolved in ether and washed with 1N sodium hydroxide and 1N hydrochloric acid. After drying over magnesium sulfate, the solvent is removed in vacuo and the residue is chromatographed in silica gel (1 kg) with ether/hexane (1:4) as the eluent to afford in succession N-t-butoxy-carbonyl-3,4-dihydro-5-methoxy-2H-[1 ]-benzothiopyran-3-amine and N-t-butoxycarbonyl-3,4-dihydro-7-methoxy-2H-[1]-benzothiopyran-3-amine.

A solution of 10 g of N-t-butoxycarbonyl-3,4-dihydro-5-methoxy-2H-[1]-benzothiopyran-3-amine in 30 ml of trifluoroacetic acid is kept at room temperature for 1 hour. The solvent is removed in vacuo, the residue is treated with 1N NaOH and the product is extracted with ether. After drying over magnesium sulfate, the solvent is removed in vacuo to afford 3,4-dihydro-5-methoxy-2H-[1]-benzothiopyran-3-amine as an oil.

EXAMPLE 4

Preparation of 2-[p-(2-carboxyethyl)-2-phenethylamino]-adenosine-5'-(N-ethyl)-carboxAmide Hydrochloride A mixture of 2.70 g of 2-[p-(2-t-butoxycarbonyl-ethyl)-2-phenethylamino]-2',3'-O-isopropylidene-a denosine-5'-(N-ethyl)-carboxamide and 45 ml of 1N hydrochloric acid is heated at 65° for 1 hour. The reaction mixture is cooled, the resulting precipitate is collected, washed first with ice water and then with a mixture of ethyl acetate and ether to yield 2-[p-(2-carboxyethyl)-2-phenethylamino]-adenosine-5'-(N-ethyl)-carboxamide hydrochloride, m.p. 200°–203° (of example 2 g);

The starting material is prepared as follows:

A mixture of 2.31 g of t-butyl p-(cyanomethyl) phenylacrylate (example 2g), 6.28 g of concentrated aqueous ammonium hydroxide and 0.46 g of 5% rhodium on alumina in 50 ml of absolute ethanol is hydrogenated at 3 atmospheres pressure and room temperature for 22 hours. A second portion of 0.46 g of rhodium on alumina is added and hydrogenation is continued for 6 more hours. The reaction mixture is filtered, the catalyst is washed with ethanol, and the filtrate is evaporated to dryness. The residue is dissolved in 50 ml of ethyl acetate, hydrogen chloride gas is bubbled into the solution for 10 minutes and the solution is evaporated to dryness. The product is triturated with ether and collected to yield p-(2-t-butoxycarbonylethyl)-2-phenethylamine hydrochloride which is then converted to the free base.

A mixture of 4.0 g of 2-chloro-2',3'-O-isopropylidene-adenosine-5'-(N-ethyl)-carboxamide and 14.0 g of p-(2-t-butoxycarbonylethyl)-2-phenethylamine is heated at 130° for 3 hours. The reaction mixture is dissolved in methylene chloride, the solution is washed with sodium bicarbonate solution and evaporated to dryness. The residue is crystallized from ether to yield 2-[p-(2-t-butoxycarbonylethyl)-2-phenethylamino] -2',3'-O-isopropylidene-ad enosine-5'-(N-ethyl)-carboxamide, m.p. 180° .

EXAMPLE 5

Preparation of 2-[p-(2-carboxyethyl)-2-phenethylamino]-3'-deoxyadenosine-'-(N-ethyl)-carboxamide A solution of 12 mg of 2β- {2-[p-(2-t-butoxycarbonyl-ethyl)-2-phenethylamino]-9-adenyl}-3-alp ha-hydroxy-2,3-dihydrofuran-5-N-ethylcarboxamide in 1.5 ml of ethanol to which is added 10 mg of 5% rhodium on carbon is hydrogenated at room temperature and 3 atmospheres pressure for 30 hours. The catalyst is filtered off and the solution is evaporated to dryness to yield a mixture of isomers comprising 2-[p-(2-carboxyethyl)-2-phenethylamino]-3'-deoxyadenosine-5'-(N-ethyl)-carboxamide; NMR ($CD_3OD$): 8.0 (s,1H), 5.93 (d,1H).

The starting material is prepared as follows:

Sodium hydride (6 mg of 60% dispersion in mineral oil) is added to a solution of 20 mg of 2-[p-(2-t-butoxycarbonylethyl)-2-phenethylamino]-2',3'-O-isopropylidene-a denosine-5'-(N-ethyl)-carboxamide in 25 ml of anhydrous isopropanol. The reaction mixture is heated at 70° for 6 hours. The reaction mixture is cooled and the reaction is quenched with 0.5 ml pH6 phosphate buffer, and the mixture is evaporated to dryness. The resulting product is chromatographed on silica gel eluting with 10% methanol in methylene chloride to yield 2- {2β-[p-(2-t-butoxycarbonyl-ethyl)-2-phenethylamino]-9-adenyl}-3-alp ha-hydroxy-2,3-dihydrofuran-5-N-ethylcarboxamide as an oil; NMR ($CD_3$ OD): 7.82 (s,1H), 6.36 (d,1H), 6.1 (d,1H), 5.52 (t,1H).

EXAMPLE 6

(a) A mixture of 1.05 g of 2- [p-(2-carboxyethyl)-2phenethylamino]-adenosine-5 '-(N-ethyl)-carboxamide sodium salt and 314 mg of ethyl iodide in 10 ml of dimethylformamide is stirred at room temperature for 16 hours. The reaction mixture is poured onto water and the product is extracted with ethyl acetate. After drying over magnesium sulfate the solvent is removed in vacuo and the residue is triturated with ether to afford 2-[p-(2)carboxyethyl)-2-phenethylamino]-adenosine-5'-(N-ethyl)-carboxamide de ethyl ester m.p. 81°–89°, the compound of formula Ia wherein $R_4$, represents ethyl, $R_5$, R6, $R_7$ and $R_8$ represent hydrogen, and $R_9$ represents p-(2-ethoxycarbonylethyl)-phenyl.

Prepared in a similar fashion are the following:

(b) 2-[p-(2-carboxyethyl)-2-phenethylamino]-adenosine5'-(N-ethyl)-carboxamide pivaloyloxymethyl ester, m.p. 85°–89°;

(c) 2-[p-(2-carboxyethyl)-2-phenethylamino]-adenosine-5'-(N-ethyl)-carboxamide methyl ester, m.p. 90°–95°;

(d) 2-[p-(2-carboxyethyl)-2-phenethylamino]-adenosine-5'-(N-ethyl)-carboxamide 2-N,N-dimethylaminoethyl ester;

(e) 2-[p-(2-carboxyethyl)-2-phenethylamino]-adenosine-5'-(N-ethyl)-carboxamide n-butyl ester, m.p. 68°–75°.

EXAMPLE 7

The following compounds can be prepared substantially according to the procedures described herein.

(a) 2-(3-cyclohexylpropylamino)-adenosine-5'-(N-ethyl)-carboxamide hydrochloride, m.p. 175°–181 °;

(b) 2-(4-cyclohexylbutylamino)-adenosine-5'-(N-ethyl) carboxamide hydrochloride, m.p. 130°–134°;

(c) 2-[2-(2-norbornanyl)-ethylamino]-adenosine-5'-N-ethylcarboxamide;

(d) 2-[2-(1-adamantyl)-ethylamino]-adenosine-5'-N-ethylcarboxamide;

(e) 2-[2-(1-cyclohexenyl)-ethylamino]-adenosine-5'-N-ethylcarboxamide;

(f) 2-[2-(tetrahydropyran-4-yl)-ethylamino]-adenosine-5'-N-ethylcarboxamide; the starting 2-(tetrahydropyran-4-yl)-ethylamine can be prepared from tetrahydropyran-4-one e.g. by Wittig condensation with diethyl cyanomethyl phosphonate followed by hydrogenation and reduction with lithium aluminum hydride.

(g) 2-(p-hydroxy-2-phenethylamino)-adenosine-5'-(N-ethyl)-carboxamide, m.p. 110°–116°.

(h) 2-(3-phenylpropylamino)-adenosine- 5'-(N-ethyl) carboxamide, hydrochloride salt, m.p. 114°–120°.

(i) 2-(4-phenylbutylamino)-adenosine- 5'-(N-ethyl) carboxamide, hydrochloride salt, m.p. 115°–120°.

(j) 2-[p-carboxyethyl)-2-phenethylamino]-adenosine-5'-(N-ethyl)-carboxamide benzyl ester, m.p. 75°–80°.

(k) 2-(β-hydroxy-p-methyl-2-phenethylamino)-adenosine-5'-(N-ethyl)-carboxamide, m.p. 124°–130°, alpha]D=+4.94° (EtOH), prepared from R(-)-β-hydroxy-β-methyl-2-phenethylamine.

(1) 2-(β-hydroxy-β-methyl-2-phenethylamino)-adenosine-5'-(N-ethyl)-carboxamide, m.p. 115°–120°, alpha]$_D$D=+29.06° (EtOH), prepared from S(+)-β-hydroxy-β-methyl-2-phenethylamine.

EXAMPLE 8

Preparation of 2-[(4-hydroxy-3-iodo)2-phenethylamino]-adenosine-5'-(N-ethyl)-carboxamide A solution of 2-hydroxy-2-phenethylamino)-adenosine-5'-(N-ethyl)-carboxamide (170 mg) in dimethylformamide (1 mL) is treated with 0.3 M aqueous disodium hydrogen phosphate (0.65 mL) followed by chloramine T hydrate (17.8 mg) and sodium iodide (117 mg). After 3 hours of stirring, chloramine-T hydrate (17.8 mg) and sodium iodide (117 mg) are again added and the whole stirred overnight. More chloramine-T (17.8 mg) is added and after a further 3 hour period, the solvent is removed under high vacuum and the residue treated with excess aqueous sodium thiosulfate and extracted with ethyl acetate. The organic extract is washed with brine, dried over sodium sulphate and chromatographed over silica gel with 10% methanol in methylene chloride as eluent. The desired fractions are combined and concentrated to dryness at reduced pressure to afford 2-[(4-hydroxy-3-iodo)2-phenethylamino]-adenosine-5'-(N-ethyl)-carboxamide, m.p. 131°–140°.

EXAMPLE 9

Preparation of 2-[p-(2-carboxyethyl)-2-phenethylamino]-2'3'-di-O-acetyl-adenosine-5'-(N-ethyl)-carboxamide Benzyl Ester A mixture of 2-[p-(2-carboxyethyl)-2-phenethylamino]-adenosine-5'-(N-ethyl)-carboxamide benzyl ester (0.4 g), pyridine (10 mL) and acetic anhydride (1 mL) is stirred at room temperature under nitrogen for 2 hours. The mixture is concentrated under high vacuum, taken up in ethyl acetate, washed with cold dilute sodium bicarbonate solution, washed with brine, dried over sodium sulfate and concentrated to dryness to afford 2-[p-(2-carboxyethyl)-2-phenethylamino]-2',3'-di-O-acetyl-adenosine-5'-(N-ethyl)-carboxamide benzyl ester as an oil.

EXAMPLE 10

Preparation of 2-[p-(2-carboxyethyl)-2-phenethylamino]-2'3'-di-O-acetyl-adenosine-5'-(N-ethyl)-carboxamide A solution of 2-[p-(2-carboxyethyl)-2-phenethylamino]-2',3'-di-O-acetyl-adenosine-5'-(N-ethyl)-carboxamide benzyl ester (0.45 g) in ethanol (100 mL) is hydrogenated at 50 p.s.i. at room temperature over 5 hours in the presence of 10% Pd on carbon (0.5 g). The mixture is filtered and the filtrate concentrated to dryness to afford 2-[p-(2-carboxyethyl)-2-phenethylamino]-2',3'-di-O-acetyl-adenosine-5'-(N-ethyl)-carboxamide, m.p. 113°–117°, [alpha]D=+5.0° (c=1.28, MeOH).

EXAMPLE 11

Prepared similarly to procedures described in examples 9 and 10 are:

(a) 2-[p-(2-carboxyethyl)-2-phenethylamino]-2',3-di-O-n-propionyl-adenosine-5'-(N-ethyl)-carboxamide;

(b) 2-carboxyethyl)-2-phenethylamino]-2',3'-di-O-butyryl-adenosine-5'-(N-ethyl )-carboxamide;

(c) 2-[p-(2-carboxyethyl)-2-phenethylamino]-2,3'-di-O-benzoyl-adenosine-5'-(N-ethyl)-carboxamide;

(d) 2-[p-(2-carboxyethyl)-2-phenethylamino]-2,3'-di-O-nicotinoyl-adenosine-5'- (N-ethyl)-carboxamide.

EXAMPLE 12

Preparation of 2-[p-(2-phenethylaminocarbonylethyl)-2-phenethylamino]-adenosine-5'-(N-ethyl)-carboxamide A mixture of 500 mg of 2-[p-(2-carboxyethyl)-2-phenethylamino]-adenosine-5'-(N-ethyl)-carboxamide, 205 mg of 1,3-dicyclohexylcarbodiimide and 122 mg of phenethylamine in 15 ml of methylene chloride is stirred overnight at room temperature. The reaction is poured into 50 ml of methylene chloride and washed with 25 ml of 10% aqueous sodium bicarbonate and 25 ml of water. The organic layer is dried over magnesium sulfate and evaporated to give a crude product which is purified by flash column chromatography using 9:1 methylene chloride-methanol saturated with ammonia to give 2-[p-(2-phenethylaminocarbonylethyl)-2-phenethylamino]-adenosine-5'-(N-ethyl)-carboxamide.

EXAMPLE 13

The following compounds of formula I wherein R and $R_2$ represent hydrogen, $R_3$ represents hydroxy and $R_4$ represents ethyl can be prepared substantially according to procedures described above.

COMPOUND $R_1$ (a) p-[2-(3-indolylethylaminocarbonyl)ethyl]-2-phenethyl
(b) p-[2-(3-morpholinopropylaminocarbonyl)ethyl]-2-phenethyl
(c) p-[2-(4-hydroxyphenethylaminocarbonyl)ethyl]-2-phenethyl
(d) p-[2-(decylaminocarbonyl)ethyl]-2-phenethyl
(e) p-{2-[5-(ethoxycarbonylpentyl)aminocarbonyl]-ethyl}-2-phenethyl
(f) p-{2-[3-(N-pyrrolidin-2-onyl)propylaminocarbonyl]-ethyl}-2-phenethyl
(g) p-[2-(4-benzylpiperidinocarbonyl)ethyl]-2-phenethyl
(h) p-[2-(4-benzylpiperazinocarbonyl)ethyl]-2-phenethyl
(i) p-[2-(3-dimethylaminopropylaminocarbonyl)ethyl]-2-phenethyl
(j) p-[2-(4-ethoxycarbonylpiperidinocarbonyl]-2-phenethyl
(k) p-[2-(4-ethoxycarbonylpiperidinocarbonyl]-2-phenethyl
(l) p-{2-[4-(2-pyridyl)-piperazinocarbonyl]ethyl}-2-phenethyl

ANALYTICAL EXAMPLES

Determination of the Degree of Activity for the Compounds

Adenosine-2 (A-2) receptor binding properties, indicative of the adenosine-2 receptor agonist activity of the compounds of the invention are determined in vitro by determining their ability to inhibit the specific binding of 3H-5'-N-ethylcarboxamidoadenosine ($^3$H-NECA), e.g. essentially as described by R. F. Bruns et al, Mol. Pharmacol. 29, 331 (1986), in striatal membrane preparations from corpus striatum of male Sprague-Dawley rats. The concentration of a particular compound required to displace the specific binding of 4 nM $^3$H-NECA is determined in the presence of 50 nM cyclopentyladenosine.

Adenosine-1 (A-1) receptor binding properties of the compounds of the invention indicative of adenosine-l-receptor agonist activity are determined, e.g., essentially according to R. F. Bruns et al in Proc. Natl. Acad. Sci. U.S.A. 77:5547 (1980), by determining their ability to inhibit the specific binding of 3 H-cyclohexyladenosine (3 H-CHA) in rat brain membrane preparations from male Sprague-Dawley rats. The concentration of a particular compound required to displace the specific binding of 1 nM $^3$H-CHA is determined.

Selectivity for the adenosine-2 (A-2) receptor can be ascertained by comparing the relative potency in the two adenosine receptor assays.

The activity of the compounds can be readily determined using no more than routine experimentation using any of the following assays.

Rat $A_1$ and $A_{2A}$ Adenosine Receptor Binding Assay
Membrane Preparations:

Male Wistar rats (200–250 g) can be decapitated and the whole brain (minus brainstem, striatum and cerebellum) dissected on ice. The brain tissues can be disrupted in a Polytron (setting 5) in 20 vols of 50 mM Tris HCl, pH 7.4. The homogenate can then be centrifuged at 48,000 g for 10 min and the pellet resuspended in Tris-HCL containing 2 IU/ml adenosine deaminase, type VI (Sigma Chemical Company, St. Louis, Mo., USA). After 30 min incubation at 37° C., the membranes can be centrifuged and the pellets stored at −70°C. Striatal tissues can be homogenized with a Polytron in 25 vol of 50 mM Tris HCL buffer containing 10 mM $MgCl_2$ pH 7.4. The homogenate can then be centrifuged at 48,000 g for 10 min at 4° C. and resuspended in Tris HCl buffer containing 2 IU/ml adenosine deaminase. After 30 min incubation at 37° C., membranes can be centrifuged and the pellet stored at −70° C.
Radioligand Binding Assays:

Binding of [$^3$H]-DPCPX (1,3-dipropyl-8-cyclopentylxanthine) to rat brain membranes can be performed essentially according to the method previously described by Bruns et al., Proc. Natl. Acad. Sci. 77, 5547–5551 1980. Displacement experiments can be performed in 0.25 ml of buffer containing 1 nM [$^3$H]-DPCPX, 100 μl of diluted membranes of rat brain (100 μg of protein/assay) and at least 6–8 different concentrations of examined compounds. Non specific binding can be determined in the presence of 10 μM of CHA ($N^6$cyclohexyladenosine) and this is always <10% of the total binding. Incubation times are typically 120 min at 25 ° C.

Binding of [$^3$H]-SCH 58261 (5-amino-7-(2-phenylethyl)-2-(2-furyl)-pyrazolo[4,3-e]-1,2,4-triazolo[1,5-c]pyrimidine) to rat striatal membranes (100 μg of protein/assay) can be performed according to methods described in Zocchi et al., J. Pharm. and Exper. Ther. 276:398–404 (1996). In competition studies, at least 6–8 different concentrations of examined compounds should be used. Non specific binding can be determined in the presence of 50 μM of NECA (5'-(N-ethylcarboxamido)adenosine). Incubation time is typically 60 min at 25 ° C.

Bound and free radioactivity can be separated by filtering the assay mixture through Whatman GF/B glass-fiber filters using a Brandel cell harvester (Gaithersburg, Md, USA). The incubation mixture can be diluted with 3 ml of ice-cold incubation buffer, rapidly vacuum filtered and the filter can be washed three times with 3 ml of incubation buffer. The filter bound radioactivity can be measured, for example, by liquid scintillation spectrometry. The protein concentration can be determined, for example, according to a Bio-Rad method (Bradford, Anal. Biochem. 72:248 (1976)) with bovine albumin as reference standard.

Human Cloned $A_3$ Adenosine Receptor Binding Assay

Receptor Binding Assays

Binding assays can be carried out according to methods described in Salvatore et al., *Proc. Natl. Acad. Sci.* 90:10365–10369 (1993). In saturation studies, an aliquot of membranes (8 mg protein/ml) from HEK-293 cells transfected with the human recombinant $A_3$ adenosine receptor (Research Biochemical International, Natick, Mass., USA) can be incubated with 10–12 different concentrations of [$^{125}$I]AB-MECA ranging from 0.1 to 5 nM. Competition experiments can be carried out in duplicate in a final volume of 100 µl in test tubes containing 0.3 nM [$^{125}$I]AB-MECA, 50 mM Tris HCL buffer, 10 mM $MgCl_2$, pH 7.4 and 20 µl of diluted membranes (12.4 mg protein/ml) and at least 6–8 different concentrations of examined ligands.

Incubation time was 60 min at 37° C., according to the results of previous time-course experiments. Bound and free radioactivity were separated by filtering the assay mixture through Whatman GF/B glass-fiber filters using a Brandel cell harvester. Non-specific binding was defined as binding in the presence of 50 µM R-PIA and was about 30% of total binding. The incubation mixture was diluted with 3 ml of ice-cold incubation buffer, rapidly vacuum filtered and the filter was washed three times with 3 ml of incubation buffer. The filter bound radioactivity was counted in a Beckman gamma 5500B γ counter. The protein concentration can be determined according to a Bio-Rad method (3) with bovine albumin as reference standard.

Data Analysis

Inhibitory binding constant, $K_i$, values can be calculated from those of $IC_{50}$ according to the Cheng & Prusoff equation (Cheng and Prusoff, *Biochem. Pharmacol.* 22:3099–3108 (1973)), $K_i = IC_{50}/(1+[C^*]/K_D^*)$, where $[C^*]$ is the concentration of the radioligand and $K_D^*$ its dissociation constant.

A weighted non linear least-squares curve fitting program LIGAND (Munson and Rodbard, *Anal. Biochem.* 107:220–239 (1990)) can be used for computer analysis of saturation and inhibition experiments. Data are typically expressed as geometric mean, with 95% or 99% confidence limits in parentheses.

Examples Demonstrating Selective Coronary Vasodilation

EXAMPLE 1

Perfusion of Isolated Guinea Pig Heart Preparations

An isolated guinea pig heart preparation can be set up using well-known techniques. The heart can be perfused with a constant flow pump through the coronary vessels with a oxygenated balanced salt solution. The coronary perfusion pressure and the EKG can be measured. Under constant flow, a decrease in coronary perfusion pressure indicates dilation ($A_{2a}$ effect). If the EKG shows decrease in heart rate or conduction velocity, this signals an $A_1$ effect. Various doses of adenosine and 2-substituted adenosine carboxamide derivatives can be given to the isolated heart, dose-response curves constructed, and the $A_{50}$ (concentration producing a 50% maximal response) can be calculated.

EXAMPLE 2

Relaxation of pre-contracted Guinea Pig Aorta

A ring cut from the guinea pig aorta can be placed in an organ bath and the tension developed by the ring measured with a force-tension transducer. It is well known that relaxation of the pre-contracted aorta by adenosine analogs indicates an $A_{2b}$ effect.

EXAMPLE 3

Cardiovascular Function Testing on an Anesthetized Dog

An anesthetized dog can be prepared for cardiovascular function testing. Electromagnetic flow probes can be placed on the circumflex coronary artery and the left anterior descending coronary artery. Systemic systolic and diastolic blood pressure and heart rate can also be measured.

Adenosine (372 µg/kg/min) and 2-substituted adenosine carboxamide derivatives can be separately infused and continuous measurements can be made of the above cardiovascular parameters. The effective dose for the compounds versus the dose for adenosine in increasing circumflex coronary blood flow can be compared, as well as the decrease in systolic blood pressure.

EXAMPLE 4

Detection of Cardiac Perfusion Deficits in Anesthetized Dogs

Dogs can be anesthetized and their circumflex coronary artery stenosed to produce a cardiac perfusion deficit. A control dog can be infused with adenosine at a dosage of about 372 µg/kg/min for about 6 minutes and then injected with thallium-201. A gamma scan will produce a scintigram which clearly shows a perfusion defect. Similarly, another dog can be infused with 2-substituted adenosine carboxamide derivatives before the thallium-201 scintigram is obtained. This dog can be evaluated for evidence of a perfusion deficit proving that 2-substituted adenosine carboxamide derivatives are suitable in this animal model of a routine clinical procedure.

Various modifications of the herein disclosed invention, in terms of structural modifications of the invented compounds and also in terms of making or using the same, may become readily apparent to those skilled in the art in light of the above disclosure. For example, the compounds of the present invention may be administered as pharmaceutically acceptable salts.

What is claimed is:

1. A method for measuring myocardial function in a mammal in need of such measurement comprising:

(a) administering to said mammal from about 0.001 to about 1 µg/kg/min of 2-substituted adenosine carboxamide derivatives as a pharmacological stressor thereby causing selective coronary vasodilation; and then (b) performing a technique on said mammal to measure myocardial function; such that myocardial function is measured while producing less systemic hypotension and reflex tachycardia compared to when adenosine is used as a pharmacological stressor.

2. The method of claim 1, wherein the 2-substituted adenosine carboxamide derivatives have the following formulas:

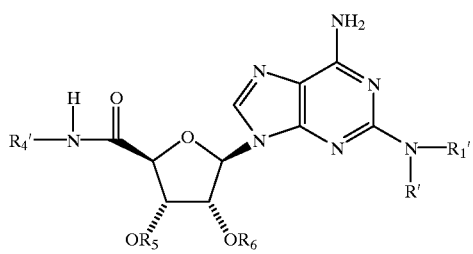

Formula I wherein R' is hydrogen or lower alkyl;

$R_1'$ is $C_3$–$C_6$-cycloalkyl optionally substituted by lower alkyl, $C_3$–$C_6$-cycloalkyl-lower alkyl optionally substituted by lower alkyl, bicycloalkyl, bicycloakyl-lower alkyl, aryl, aryl-lower alkyl-$C_3$–$C_6$-cycloalkyl, 9-fluorenyl, diary-lower alkyl, 9-fluorenyl-lower alkyl, cycloalkenyl-lower alkyl, bicycloalkenyl-lower alkyl, tetrahydropyranyl-lower alkyl, tetrahydrothio-pyranyl-lower alkyl or adamantyl-lower alkyl: of $R_1$ is a bicyclic benzo-fused 5- or 6-membered saturated carbocyclic radical or a benzo-fused 5- or 6-membered saturated heterocyclic radical containing a heteroatom selected from oxygen and sulfur which is directly attached to the fused benzene ring, any said bicyclic radical being unsubstituted or substituted on the benzo portion by lower alkyl, lower alkoxy, hydroxy, halogen or trifluoromethyl, or by a substituent —W—Z in which W is a direct bond, lower alkylene, lower alkenylene, thio-lower alkylene or oxy-lower alkylene and Z is cyano, carboxy or carboxy derivatized in the form of a pharmaceutically acceptable ester or amide, or $R_1'$ is any said bicyclic radical substituted-lower alkyl;

or $R_1'$ is aryl-hydroxy lower alkyl;

$R_2$ is hydrogen, lower alkyl or aryl-lower alkyl;

$R_3$ is hydrogen or hydroxy;

$R_4$ is hydrogen, lower alkyl, aryl-lower alkyl, $C_3$–$C_6$-cycloalkyl or hydroxy-lower alkyl; aryl is an optionally substituted carbocyclic aromatic radical, being preferably 1- or 2-naphthyl, phenyl, or naphthyl or phenyl substituted by one to three of lower alkyl, lower alkoxy, hydroxy, halogen or trifluoromethyl, or naphthyl or phenyl substituted by a substituent —W—Z in which W is a direct bond, lower alkylene, lower alkenylene, thio-lower alkylene or oxy-lower alkylene and Z is cyano, carboxy or carboxy derivatized in the form of a pharmaceutically acceptable ester or amide; or aryl is a heterocyclic aromatic radical, being preferably pyridyl or thienyl, each optionally substituted as described above for phenyl; pharmaceutically acceptable ester derivatives thereof in which free hydroxy groups are esterified in the form of a pharmaceutically acceptable ester;

and pharmaceutically acceptable salts thereof,

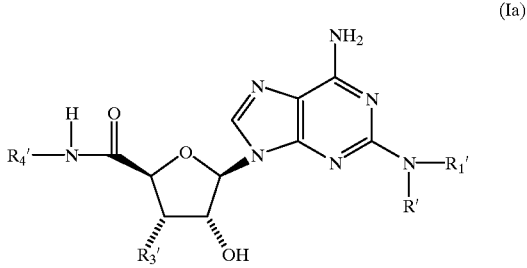

Formula (Ia)

wherein R' is hydrogen or lower alkyl;

$R_1'$ is $C_3$–$C_6$-cycloalkyl-lower alkyl; or $R_1'$ is aryl-lower alkyl in which aryl is thienyl, pyridyl, phenyl or phenyl monosubstituted by halogen, trifluoromethyl, lower alkoxy, hydroxy, lower alkyl, or by a substituent —W—Z in which W is a direct bond, lower alkylene, thio-lower alkylene or oxy-lower alkylene, and Z is cyano, carboxy, lower alkoxycarbonyl, carbamoyl, N-mono- or N,N-di-lower alkylcarbamoyl; or R1' is a substituent of the formula B'

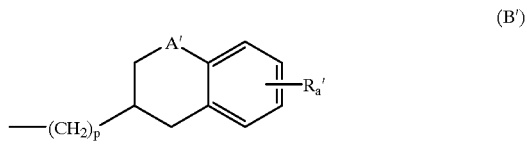

in which A' is a direct bond, methylene, oxy or thio, p is zero, one or two and $R_a'$ is hydrogen, lower alkyl, lower alkoxy, hydroxy, halogen or —W—Z as defined above; or $R_1'$ is aryl-hydroxy-lower alkyl in which aryl has meaning as defined above;

$R_3'$ is hydrogen or hydroxy; and $R_4'$ is hydrogen, lower alkyl, $C_3$–$C_6$-cycloalkyl or hydroxy-lower alkyl;

pharmaceutically acceptable prodrug ester derivatives thereof in which one or more free hydroxy groups are esterified in the form of a pharmaceutically acceptable ester; and pharmaceutically acceptable salts thereof,

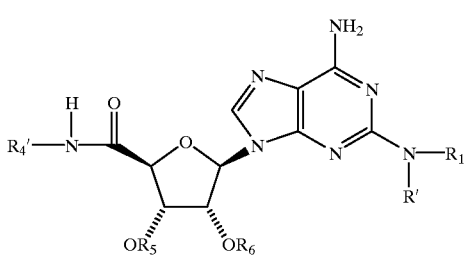

Formula II wherein R' is hydrogen or $C_1$–$C_4$-alkyl; $R_1'$ is ($C_5$- or $C_6$)-cycloalkyl-$C_1$–$C_4$-alkyl, or $R_1'$ is aryl-$C_1$–$C_4$-alkyl in which aryl is 2- or 3-thienyl, 2-, 3- or 4-pyridyl, phenyl, or phenyl monosubstituted by halogen, trifluoromethyl, lower alkoxy, lower alkyl or by a substituent —W—Z in which W is a direct bond, $C_1$–$C_4$-alkylene, thio-$C_1$–$C_3$-alkylene or oxy-$C_1$–$C_3$-alkylene and Z is cyano, carboxy, lower alkoxycarbonyl, carbamoyl, N-mono- or N,N-di-lower alkylcarbamoyl; or $R_1'$ is aryl-hydroxy-$C_1$–$C_4$-alkyl in which aryl has meaning as defined above;

$R_4'$ is $C_1$–$C_4$-alkyl, cyclopropyl or hydroxy-$C_2$–$C_4$-alkyl;

$R_5$ and $R_6$ are hydrogen, lower alkanoyl, lower alkoxy-lower alkanoyl, aroyl, carbamoyl, mono- or di-lower alkylcarbamoyl; and pharmaceutically acceptable salts thereof, (IIa)

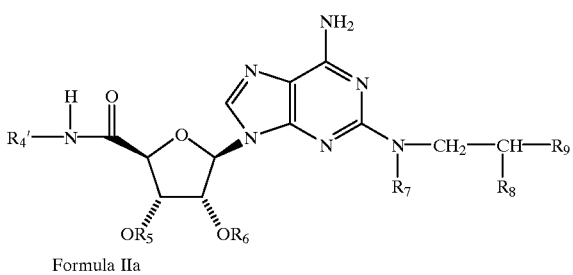

Formula IIa wherein $R_4'$ is ethyl;

$R_5$ and R6 are hydrogen or lower alkanoyl;

$R_7$ is hydrogen or methyl;

$R_8$ is hydrogen or methyl;

$R_9$ is cyclohexyl, phenyl, or phenyl monosubstituted by halogen, trifluoromethyl, lower alkyl, lower alkoxy or —$CH_2$ $CH_2$—Z in which Z is carboxy or lower alkoxycarbonyl; and pharmaceutically acceptable salts thereof.

3. The method of claim 1, wherein the 2-substituted adenosine carboxamide derivatives are administered in a parenteral dosage form.

4. The method of claim 1 wherein said technique comprises administering an imaging agent to said mammal, and thereafter imaging said mammal.

5. The method of claim 1 wherein about 0.1 μg/kg/min to about 1 μg/kg/min of the 2-substituted adenosine carboxamide derivatives are administered.

6. The method of claim 1, wherein the compound is ((2-p-carboxyethyl)phenylamino-5'-N-carboxamidoadenosine).

7. The method of claim 2, wherein the compounds are of formula I, and wherein:

R is hydrogen or lower alkyl;

$R_1$ is $C_3$–$C_6$-cycloalkyl-lower alkyl;

or $R_1$ is aryl-lower alkyl wherein aryl is pyridyl, thienyl, naphthyl, phenyl, phenyl substituted by one or two substituents selected from halogen, trifluoromethyl, lower alkoxy, hydroxy and lower alkyl, or phenyl substituted by a substituent —W—Z in which W is a direct bond, lower alkylene, lower alkenylene, thio-lower alkylene or oxy-lower alkylene, and Z is cyano, carboxy, carboxy derivatized in the form of a pharmaceutically acceptable ester or carboxy derivatized in the form of a pharmaceutically acceptable amide; or $R_1$ is a substituent of the formula B

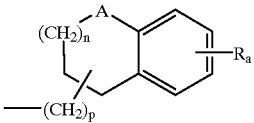

(B)

in which:

A is methylene, oxy or thio, n is zero or one, p is zero, one or two, and $R_a$ is hydrogen, lower alkyl, lower alkoxy, halogen or —W—Z as defined above;

$R_2$ is hydrogen or lower alkyl;

$R_3$ is hydrogen or hydroxy;

$R_4$ is hydrogen, lower alkyl, $C_3$–$C_6$-cycloalkyl, hydroxy-lower alkyl, or aryl-lower alkyl in which aryl is pyridyl, thienyl or phenyl;

pharmaceutically acceptable ester derivatives thereof in which one or more free hydroxy groups are esterified in the form of a pharmaceutically acceptable ester; and pharmaceutically acceptable salts thereof.

8. The method of claim 2, wherein the compounds are compounds of formula I and Ia $R_3$ and $R_3'$, respectively, are hydroxy, and ester derivatives thereof.

9. The method of claim 2, wherein the compounds are compounds of formula Ia above wherein:

$R_3'$ is hydroxy;

$R_4'$ is lower alkyl, cyclopropyl or hydroxy-lower alkyl;

pharmaceutically acceptable prodrug ester derivatives thereof in which free hydroxy groups are esterified in the form of a pharmaceutically acceptable ester;

and pharmaceutically acceptable salts thereof.

10. The method of claim 2 wherein the compounds are compounds of formula II wherein R' is $C_1$–$C_3$-alkyl or hydrogen; $R_1'$ is $CH_2$ $CH_2$-(cyclohexyl or cyclopentyl); or $R_1'$ is —$CH_2$ $CH_2$-aryl in which aryl is 2- or 3-pyridyl, phenyl, or phenyl monosubstituted by a substituent —$CH_2$ $CH_2$—Z or —$OCH_2$—Z in which Z is cyano, carboxy, lower alkoxycarbonyl, carbamoyl, N-mono-or N,N-di-lower alkylcarbamoyl;

$R_4'$ is ethyl or hydroxyethyl;

$R_5$ and $R_6$ are hydrogen, lower alkanoyl or lower alkoxy-$C_2$–$C_4$-alkanoyl; and pharmaceutically acceptable salts thereof.

11. The method of claim 2 wherein the compounds are compounds of formula II wherein R' is hydrogen or methyl; $R_1'$ is cyclohexylethyl; or $R_1'$ is 2-phenylethyl, 2-(2-pyridyl)-ethyl or 2-phenylethyl substituted in the para position by $CH_2$ $CH_2$ Z in which Z is carboxy, lower alkoxycarbonyl, carbamoyl or mono-lower alkylcarbamoyl:

$R_4'$ is ethyl:

$R_5$ and R6 are hydrogen; and pharmaceutically acceptable salts thereof.

12. The method of claim 2 wherein in formula I, R is hydrogen, in formula Ia, R' is hydrogen, in formula II, R' is hydrogen and in formula IIa, $R_7$ is hydrogen.

* * * * *